United States Patent [19]

Morabito et al.

[11] Patent Number: 4,962,042
[45] Date of Patent: Oct. 9, 1990

[54] METHOD FOR ON-COLUMN INJECTION GAS CHROMATOGRAPHY

[75] Inventors: Paul L. Morabito; Richard G. Melcher; Joseph F. Hiller; Terrence McCabe, all of Midland, Mich.

[73] Assignee: The Dow Chemical Company, Midland, Mich.

[21] Appl. No.: 448,410

[22] Filed: Dec. 8, 1989

Related U.S. Application Data

[63] Continuation-in-part of Ser. No. 198,425, May 25, 1988, abandoned.

[51] Int. Cl.$^5$ .............................................. G01N 31/08
[52] U.S. Cl. ...................................... 436/161; 422/89; 73/23.42; 55/67; 55/197; 55/386
[58] Field of Search ....................... 436/161, 167, 168; 422/89; 73/23.1; 55/67, 386, 197, 98, 432

[56] References Cited

U.S. PATENT DOCUMENTS

| | | | |
|---|---|---|---|
| 4,805,441 | 2/1989 | Sides et al. | 422/89 X |
| 4,829,008 | 5/1989 | Zaromb | 436/161 X |
| 4,872,334 | 10/1989 | Watanabe | 73/23.1 |

Primary Examiner—Robert J. Warden
Assistant Examiner—Lynn M. Kummert
Attorney, Agent, or Firm—Timothy S. Stevens

[57] ABSTRACT

In one embodiment the invention is a method for on-column valved injection gas chromatography by on-column injecting more than 5 microliters and less than one milliliter of sample consisting of a solvent and a component of interest into a retention gap/capiliary column system with an injection valve at a first carrier gas flow rate, followed by a substantially higher carrier gas flow rate to blow the solvent of the sample out of the system at a rapidly increased rate and then a return to a lower flow rate to chromatograph the component of interest. In another embodiment, less than 5 microliters of sample consisting of a solvent and a component of interest is on-column injected into a capillary column using an injection valve and a relatively high column inlet pressure of gas to move the sample from the injection valve into the colunm rapidly and with reduced carryover. Then, the pressure of carrier gas is reduced to a normal pressure for chromatography of the component of interest.

11 Claims, 3 Drawing Sheets

METHOD FOR ON-COLUMN INJECTION GAS CHROMATOGRAPHY

CROSS-REFERENCE TO RELATED APPLICATION

This application is a continuation-in-part of the copending application Ser. No. 198,425, filed May 5, 1988 abandoned.

FIELD OF THE INVENTION

The invention is in the field of on-column injection gas chromatography.

BACKGROUND OF THE INVENTION

Gas Chromatography (GC) is one of the most important tools used in chemical analysis Recently, GC has been advanced by the development of fused silica bonded stationary phase capillary columns. These columns can be used to generate chromatograms showing both high speed of analysis and high resolving power relative to the previously used packed GC columns. In addition, these columns are much less likely to be broken during normal handling than ordinary glass capillary columns.

Many sample injection techniques are used in GC such as split, splitless, flash and on-column injection. The on-column technique has several advantages and is characterized by the injection of a liquid sample directly into the inlet of a GC column. A fused silica bonded stationary phase capillary column is ideal for on-column injection because the stationary phase is chemically bonded to the interior surface of the capillary column and can not be washed off by the liquid sample. On-column injections into fused silica bonded stationary phase capillary columns using syringes having long, fine stainless steel or fused silica needles are routinely made. However, this on-column technique is not easily automated and the needles are frequently damaged in use. When very large on-column injections are made, e.g., greater than 5 microliters, the fused silica bonded stationary phase capillary column is generally preceded by a retention gap which is simply a section of fused silica capillary tubing that is usually deactivated but not coated with a stationary phase and the injection is made into the retention gap.

Steele and Vassilaros, *Journal of High Resolution Chromatography & Chromatography Communications.* Vol. 6, 1983, pp. 561–563, advanced the art of on-column injection with fused silica bonded stationary phase capillary columns by injecting a predetermined volume (1 microliter) of a sample with a loop-type rotary injection valve. A problem with the system of Steele and Vassilaros was sample carryover, i.e., not all of the sample is moved from the injection valve into the column when the valve is rotated to the inject position and the portion that remains tends to contaminate the next injection. Another problem with the system of Steele and Vassilaros occurs when the volume of sample is very large, e.g., more than 5 microliters to as much as several hundred microliters, and a retention gap is used. This problem is the long length of time needed for the solvent peak to elute.

Hopper, *Journal of Chromatography,* Vol. 302, 1984, pp. 205–219, used a rotary ten-port valve for on-column injection using both fused silica capillary columns and packed columns. The ten-port valve of Hopper incorporated a wash loop (1 microliter) in addition to a sample loop (2 microliters) so that solvent in the wash loop followed the sample onto the column to reduce the problem of sample carryover. Although the valve of Hopper does help solve the problem of sample carryover, it does so with an increased complexity of the system, i.e., a more complex valve and the use of the wash solvent. In addition, the system of Hopper when used for very large injections with a retention gap still suffers from the long length of time needed for the solvent peak to elute. Nevertheless, the rotary injection valves of Steele et al. and Hopper eliminated the use of a fragile syringe needle and made it possible to automate the injections.

SUMMARY OF THE INVENTION

The present invention is a solution to the above-stated problem of sample carryover and the long length of time needed for the solvent peak to elute for such on-column GC injection methods employing injection valves. In one embodiment, suitable for injection volumes of more than 5 microliters and less than 1 milliliter with the use of a retention gap, the sample is moved into the retention gap with gas at a first flow rate and then the flow rate of gas is temporarily increased at least 50% in less than about one second to reduce the elution time of the solvent peak. Then the flow rate of gas is decreased at least 50%. A particularly useful variant of this embodiment is to make an extract of a sample for on-column valved injection by exposing one side of a two-sided membrane to a sample and by exposing the other side of the membrane to an extractant so that a component of interest in the sample permeates through the membrane into the extractant and then is moved to the injection valve. In another embodiment, suitable for injection volumes of less than 5 microliters, the sample is moved into a capillary column system simultaneously with a temporarily at least 50% increased pressure of carrier gas in less than about one second to reduce sample carryover.

DETAILED DESCRIPTION OF THE INVENTION

Figure 1:
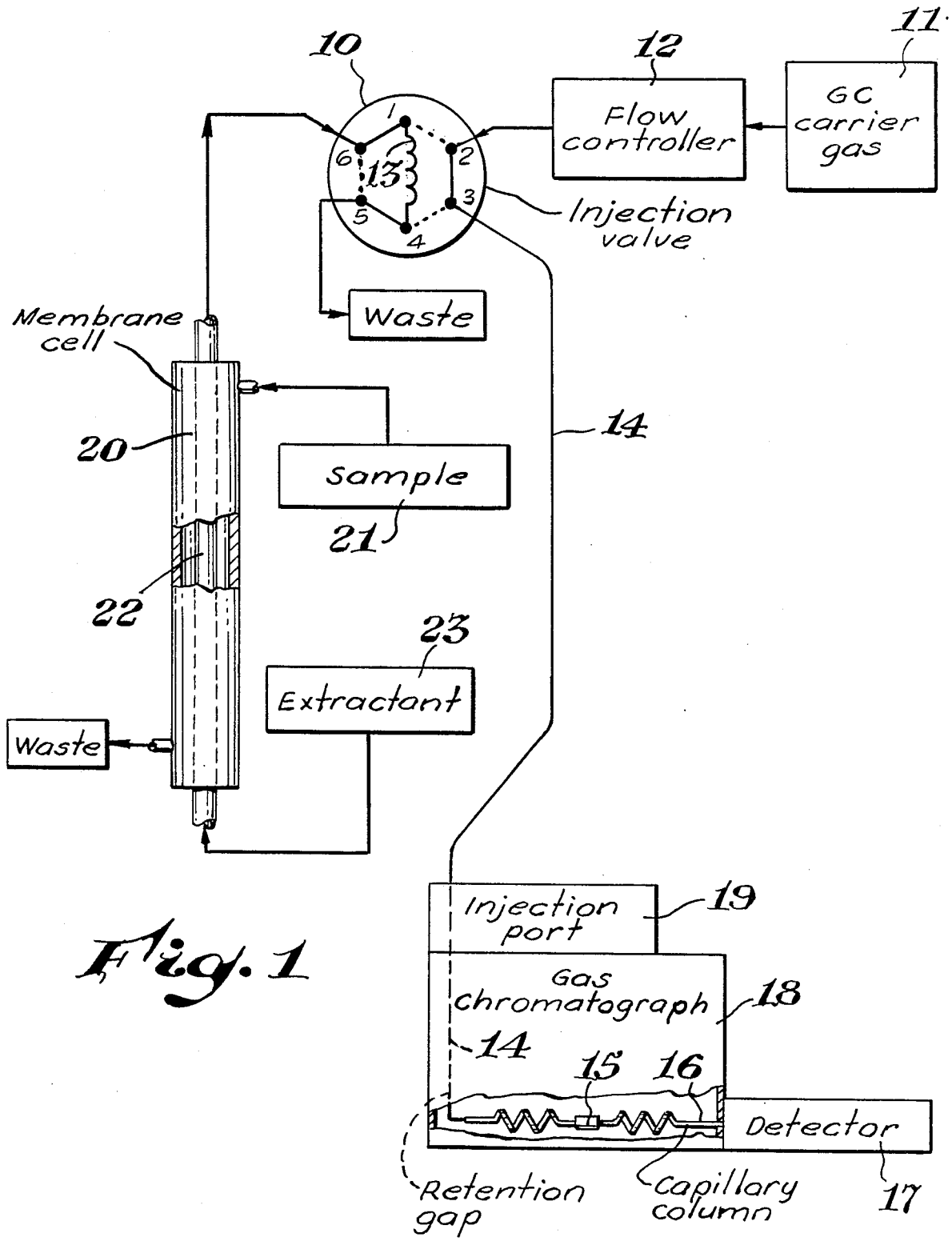
FIG. 1 is a schematic drawing of an apparatus for carrying out a method embodiment of the present invention wherein after the liquid sample is moved into the retention gap, the carrier gas flow rate is temporarily increased to shorten analysis time.

Referring now to FIG. 1 therein is shown a schematic drawing of an apparatus for carrying out a method embodiment of the present invention, including a two position six-port rotary injection valve 10 having ports 1–6. The ports 1 and 6, 5 and 4, and 3 and 2 are connected in one position of the valve 10; and the ports 1 and 2, 3 and 4, and 5 and 6 are connected in the other position of the valve 10. A sample loop 13 is connected across ports 1 and 4. A source of compressed GC carrier gas 11, such as helium or hydrogen, is shown connected to a GC carrier gas flow controller 12 such as a Porter Mass Flow Controller. Preferably, the valve 10 and the flow controller 12 are automatically controlled via a recording integrator such as a Spectrophysics 4270 or a data system computer such as a Nelson Analytical Model 3000 Chromatography Data System. The inlet end of a fused silica retention gap 14 is connected to port 3 of the valve 10. The other end of the retention gap 14 is shown connected to a butt union 15. The inlet end of a fused silica capillary column 16 is also connected to the butt union 15 and the outlet end of the column 16 is connected to a gas chromatography detector 17. The majority of the retention gap 14 and the capillary column 16 are shown within a gas chromatograph 18. The gas chromatograph 18 is shown having an injection port 19, and for convenience, the inlet end of the retention gap 14 is routed through the injection port 19 rather than through a wall of the gas chromatograph 18. The heater of the injection port 19 can thus be used to warm the retention gap within it. Preferably, the unheated length of retention gap between the injection port 19 and the valve 10 is as short as possible and thermal insulation is packed around the exposed unheated length of retention gap.

A membrane cell 20 is shown in FIG. 1 and is used to obtain an extract of a liquid sample 21 which is flowed around the outside of a tubular membrane 22 within the cell 20. An extractant 23 is flowed inside the tubular membrane 22 to port 6 of the valve 10, through the loop 13 and then to waste. A component of the sample permeates through the membrane 22 into the extractant 23. Beneficially, some components of the sample such as suspended solids, e.g., sand, do not permeate through the membrane. The extractant is typically hexane or other such volatile solvent. The sample matrix is typically water such as an aqueous waste stream. Thus, by this technique it is possible to automatically extract an aqueous sample for analysis by GC. By stopping flow of extractant 23 inside the membrane 22 for a period of time while continuing to flow the sample 21 around the outside of the membrane 22, it can be possible to concentrate a component of interest in the extractant and then move it into the loop 13 for injection.

Figure 3:
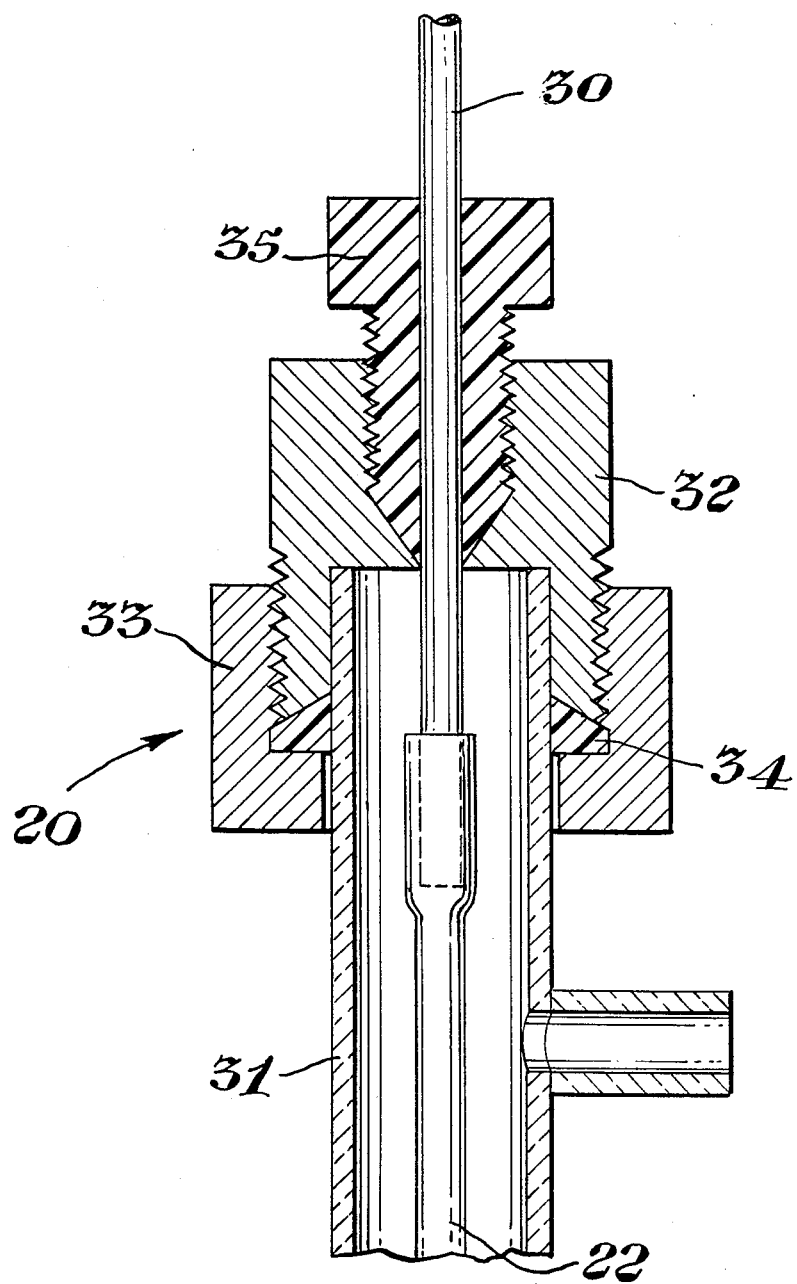
FIG. 3 is a side view, mostly in section and partly in full, of one end of the membrane cell shown schematically in FIG. 1.

In FIG. 3 is shown a side view, mostly in section and partly in full, of one end of the membrane cell 20 shown schematically in FIG. 1. One end of the tubular membrane 22 is shown stretched over a 1/16 inch outside diameter stainless steel tube 30. The membrane 22 is shown inside a necked ¼ inch outside diameter glass tube 31. A ¼ inch liquid chromatography column end fitting 32 is shown attached to the end of the tube 31 using a tubing nut 33 and a TEFLON ® ferrule 34. A FINGERTIGHT fitting 35 (available from Upchurch Scientific, Oak Harbor, Wash.) allows the tube 30 to be positioned axially to take up any slack in the membrane 22 if it swells from contact with the extractant and even allows the membrane 22 to be stretched lengthwise.

Figure 2:
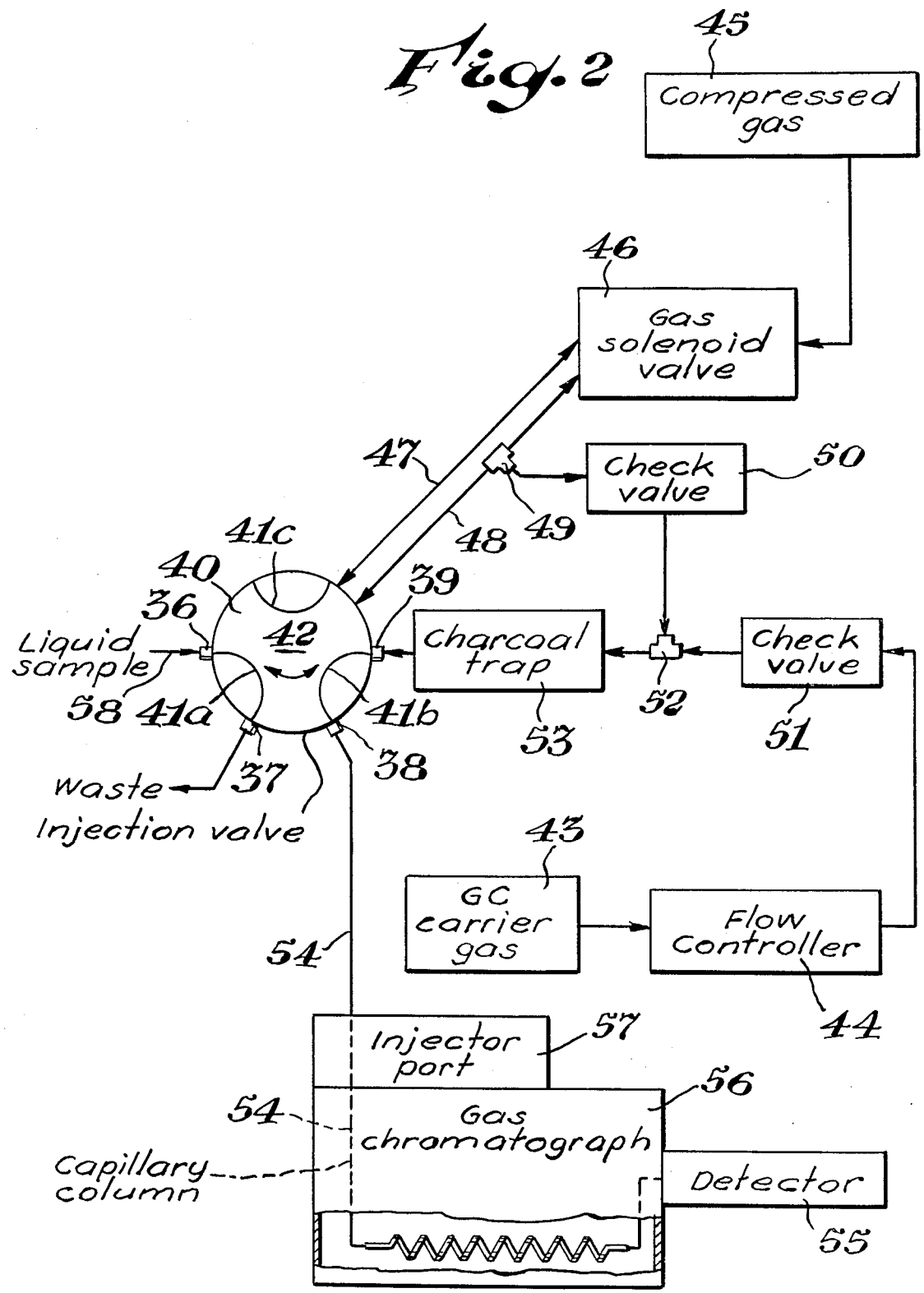
FIG. 2 is a schematic drawing of another apparatus for carrying out another method embodiment of the present invention wherein the gas used to operate the injection valve is also used to simultaneously increase the gas pressure to the capillary column.

The apparatus shown in FIGS. 1 and 2 can be used to carry out a method embodiment of a present invention for on-column valved injection gas chromatography with reduced analysis time. GC carrier gas 11 is flowed at a first flow rate by the flow controller 12 through the injection valve 10, the retention gap 14, the capillary column 16 and the detector 17. Extractant 23 is flowed into contact with one side (the inside) of the two-sided tubular membrane 22 and then through the injection valve 10 filling the loop 13. The loop 13 has an internal volume of at least 5 microliters. The upper limit of the internal volume of the loop 13 is dependent on the internal diameter and length of the retention gap 14. Injections of as much as 250 microliters have been made and larger injections such as 1 milliliter are contemplated. Sample 21 containing a component of interest is flowed into contact with the other side (the outside) of the membrane 22 and then to waste. The component of interest permeates the membrane 22 and enters the stream of extractant flowing through the valve 10 as shown. When the valve 10 is changed from the position shown by the solid lines between the ports of the valve 10 to the position shown by the dotted lines between the valve 10, the sample extract in the loop 13 is on-column injected into the retention gap 14 by the flow of carrier gas 11. Then, after an equilibration time, e.g., 15 seconds with a 50 microliter injection and 90 seconds with a 200 microliter injection, the flow controller 12 is adjusted so that the flow of carrier gas 11 through the valve 10, the retention gap 14, the column 16 and the detector 17 is substantially increased in less than one second, i.e., by at least 50% in less than one second, to a second flow rate so that at least 50% of the solvent of the sample extract (in the form of vaporized solvent) is blown through the retention gap 14, the column 16 and the detector 17 before the flow rate of carrier gas 11 is substantially reduced, i.e., by at least 50%, to a third flow rate by again adjusting the flow controller 12. With the carrier gas at the third flow rate, the temperature of the oven of the gas chromatograph 18 can be increased so that the component of interest moves from the retention gap 14 to the head of the column 16. As the oven temperature increases further, the component of interest begins to move through the column 16 and eventually emerges from the column 16 to be detected by the detector 17. Preferably, the second flow rate is maintained until substantially all of the solvent is blown out of the system. Preferably, the third flow rate is more than two times lower than the second flow rate so that the solvent is blown out of the system at an appreciably faster rate. Most preferably, the first and third flow rates are substantially the same for the sake of simplicity. Preferably, the membrane 22 is silicone rubber. However, the membrane 22 can be other rubbers and can be other polymers. Of course, a sample can be loaded directly into port 6 of the valve 10 without undergoing an extraction. However, the apparatus shown in FIG. 1 has been shown to be especially suitable for environmental analysis with high sensitivity (a very large injection) and high selectivity (the membrane/extractant system rejecting some unwanted and interfering components). It should be understood that the apparatus shown in FIG. 1 is but one that can be used to carry out this method embodiment of the present invention. For example, the flow controller 44 can be a pressure regulation device.

Referring now to FIG. 2, therein is shown a schematic drawing of an apparatus for carrying out another method embodiment of the present invention, including a gas-operated, two-position, four-port rotary injection valve 40 having ports 36–39. The ports 36 and 37, and 38 and 39 are internally connected by the channels 41a, 41b and 41c, in the rotor 42 of the valve 40. A source of compressed GC carrier gas 43 is shown connected to a GC carrier gas flow controller 44, such as a Porter Mass Flow Controller. The flow controller 44 is shown connected to a check valve 51 which is in turn connected to a tee 52, a charcoal trap 53, and the port 39 of the valve 40. The port 38 of the valve 40 is connected to the inlet end of a capillary GC column 54. The outlet end of the column 54 is connected to a GC detector 55. Most of the column 54 is contained in a gas chromatograph 56 and the column 54 conveniently enters the gas chromatograph 56 via an injector port 57. Liquid sample 58 consisting of a solvent and a sample component of interest enters the port 36 of the valve 40, fills the channel 41a and then exits port 37 of the valve 40 to waste. A source of compressed gas, such as compressed nitrogen, helium or hydrogen (preferably, the same as the carrier gas 43), is shown connected to a gas solenoid valve 46. The pressure of the compressed gas 45 must be higher than the carrier gas pressure from the flow controller 44 for reasons to be discussed below. The gas solenoid valve 46 facilitates the positioning of the gas-operated injection valve 40 by way of a tube 47 and a tube 48. When gas is sent through the tube 47, the valve 40 is positioned as shown in FIG. 2. When gas is sent through the tube 48, the rotor 42 of the valve 40 rotates counterclockwise so that the channel 41a connects the ports 38 and 39. A tee 49 in the tube 48 also directs some of this gas to a check valve 50 which is connected to the tee 52. Preferably, the solenoid valve 46 and the flow controller 44 are automatically controlled via a recording integrator such as a Spectrophysics 4270 or a data system computer such as a Nelson Analytical Model 3000 Chromatography Data System.

The apparatus shown in FIG. 2 can be used to carry out another method embodiment of a present invention for on-column valved injection gas chromatography with reduced carryover. GC carrier gas 43 is flowed at a first pressure, e.g., 10 psig, by the flow controller 44 through the check valve 51, the tee 52, the charcoal trap 53, the valve 40, the fused silica capillary column 54 and the detector 55. A predetermined volume of liquid sample 58 is contained within the channel 41a in the rotor 42 of the valve 40. The predetermined volume of the channel 41a is determined by the dimensions of the channel 41a and is less than 5 microliters (for injections of more than 5 microliters another method embodiment of the present invention is used). When the rotor 42 of the valve 40 is rotated by gas flowing through the tube 48, the gas pressure in check valve 50 is suddenly higher than the gas pressure in check valve 51. Therefore, the check valve 51 closes and the check valve 50 opens allowing gas to flow at a second pressure, e.g., 50 psig, through the trap 53, the valve 40, the column 54 and the detector 55. This second pressure is substantially higher, i.e., at least 50 percent higher in less than one second, than the first pressure and this higher pressure moves the sample contained in the channel 41a into the inlet end of the column 54 at a substantially increased rate than if the first pressure of carrier gas had been maintained when the rotor 42 was turned. So injecting the sample results in reduced sample carryover. The gas solenoid valve is then actuated, e.g., two seconds later, to send gas through pipe 47 and to relieve the gas pressure in pipe 48 to rotate the rotor 42 in a clockwise direction to the position shown in FIG. 2. When this is done the check valve 50 closes and the check valve 51 opens and carrier gas again flows from the flow controller 44 at a third pressure substantially lower, i.e., at least 50 percent lower than the second pressure With the carrier gas at the third pressure the component of interest is chromatographed under isothermal or temperature programmed conditions as is well understood by the art. Preferably, the third pressure is more than two times lower than the second pressure so that the sample is injected at an appreciably faster rate. Most preferably, the first and third pressures are substantially the same for the sake of simplicity. The charcoal trap 53 removes impurities present in the compressed gas 45 or picked up from the solenoid valve 46. It should be understood that the apparatus shown in FIG. 2 is but one that could be used to carry out this embodiment of the present invention. The use of the check valves 50 and 51 is not critical and instead the flow controller 44 could have simply been adjusted to give a higher flow when the valve 40 was operated. The apparatus shown in FIG. 1 could also be used if the loop 13 were less than 5 microliters or if the valve 40 were exchanged for the valve 10. In FIG. 2 the capillary column does not have a retention gap. However, a retention gap could have been used. Here and in the claims a "capillary column system" means a capillary column alone or a capillary column and a retention gap together.

EXAMPLE 1

The system generally shown in FIG. 1 is assembled and includes a Hewlett Packard 5890 gas chromatograph 18 equipped with an electron capture detector 17, a 30 meter long by 0.53 mm internal diameter fused silica retention gap 14 (Restek Corp., Bellefonte, Pa.) connected to a 30 meter long by 0.32 mm internal diameter fused silica capillary column 16 having a DB-5 stationary phase with a film thickness of 1 micrometer (J&W Scientific, Folsom, Calif.) a Valco 6-port valve 10 having a 200 microliter sample loop 13 and a Nelson Analytical Model 3000 Chromatography Data System. The carrier gas 11 is helium at a first and third flow rates of 8 milliliters per minute as determined by the flow controller 12. A makeup gas flow at the detector 17 of 30 milliliters of nitrogen is used.

A membrane cell 20 is assembled as shown generally in FIG. 3. A 330 mm long by 2 mm inside diameter glass tube 31 is provided with the end fittings 32/33/34/35 and Dow Corning Silastic ® Brand silicone rubber medical tubing is used as the membrane 22 having an unstretched inside diameter of 0.02 inches, an outside diameter of 0.037 inches and length of 160 mm. The silicone rubber tubing is swelled with xylene as an aid in connecting it with the 1/16 inch stainless steel tubing 30. When the xylene evaporates, the membrane shrinks back to its original dimensions and forms a tight seal to the tube 30.

The extractant 23 is hexane and is pumped at a flow rate of 0.1 milliliter per minute with a Kratos Model 400 LC pump. The sample 21 is water containing components of interest and is pumped with an FMI Jr. Lab Pump at a flow rate of 3 milliliters per minute. The hexane swells the membrane 20 and as this happens, the fitting 35 is loosened to allow the tubing 30 to be retracted from the cell 20. After about 15 minutes the system is equilibrated and the fitting 35 is finally tightened. The sample contains 3.8 parts per billion by weight (ppb) of 1,2-dichlorobenzene, 4.5 ppb 1,2,4-trichlorobenzene, 3.7 ppb 1,2,3,4-tetrachlorobenzene and 4.3 ppb pentachlorobenzene as the components of interest. These components of interest permeate through the membrane 22 into the hexane extractant and are then carried through the loop 13. When the valve 10 is changed to its inject position, the analysis program is started by the Nelson System. The extracted sample in the loop 13 is on-column injected into the retention gap 14 and ninety seconds later the flow controller 12 is adjusted to deliver a second flow rate of 32 milliliters per minute for 5 minutes and then to a third flow rate of 8 milliliters per minute for the remainder of the analysis. The oven temperature of the gas chromatograph 18 is programmed at 70 degrees centigrade for 6 minutes and then to rise at 10 degrees centigrade per minute to 240 degrees centigrade.

The components of interest elute from the column 16 to be detected by the detector 17 at about 14, 6, 18 and 20 minutes respectively with detection limits of about 500, 400, 400 and 370 parts per trillion by weight in the sample 21.

EXAMPLE 2

The same system as in Example 1 is used except an additional valve (a Rheodyne Model 7040 two position 4-way valve, Rheodyne Inc., Cotati, Calif.) is used to connect the cell 20 with the valve 10 and the extractant 23. In one 4-way valve position, the extractant flows through the membrane to the valve 10. In the other 4-way valve position, extractant flow bypasses the cell 20 and flows directly to the valve 10 while the extractant in the membrane 22 continues to receive extracted components of interest across the membrane 22. The sample 21 is flowed for 20 minutes while the extractant flow bypasses the cell 20. There are about 125 microliters of extractant in the bore of the membrane 22. Then the 4-way valve is changed to its other position and the 125 microliters of extractant are moved into the loop 13 and then the valve 10 is changed to its inject position to begin the above-mentioned analysis cycle. Because the extractant is stationary in the membrane 22 for twenty minutes, it extracts more of the components of interest from the sample 21 across the membrane 22 and now the detection limits are about 30, 10, 10, and 5 parts per trillion respectively for the components of interest in the sample 21.

EXAMPLE 3

The system generally shown in FIG. 2 is assembled and includes a Hewlett Packard 5890 gas chromatograph 56 having an electron capture detector 55. The column 54 is a 15 meter long fused silica capillary column having an internal diameter of 0.53 mm and a DB-5 stationary phase 1 micrometer thick (J&W Scientific). The valve 40 is a Valco 4-port internal slot rotary valve with a 1 microliter internal slot volume (Catalog No. A214UWP1). A Nelson Analytical Model 3000 Chromatography Data System is used to control an Asco 4-way solenoid valve 46. The carrier gas is helium at a column head pressure of about 10 psig which results in a carrier gas flow rate of about 5 milliliters per minute. At the detector 55, nitrogen makeup gas at a flow rate of 30 milliliters per minute is used. The check valves 50 and 51 are Nupro Catalog No. B-2C-TRC1-1, 1 psig activated. The flow controller 44 is a Porter Mass Flow Meter. An Anspec Catalog No. A3367 charcoal trap 53 is used. The compressed gas 45 is helium at a pressure of 55 psig. The oven of the gas chromatograph 56 is programmed to be 40 degrees centigrade for three minutes and then to rise at a rate of 15 degrees centigrade per minute to a temperature of 100 degrees centigrade and then at a rate of 6 degrees centigrade per minute to a temperature of 220 degrees centigrade.

The sample is hexane containing 50 parts per billion chlorpyrifos by weight. The sample is loaded into the valve 40, the Nelson system turns on the solenoid valve 46 and the sample within the channel 41a is injected into the column 54 at a pressure of about 55 psig. Two seconds later, the Nelson system turns off the solenoid valve 46 and the column head pressure returns to about 10 psig. The chlorpyrifos elutes from the column 54 and is detected by the detector 55 as a chromatographic peak of a given area. Another sample containing only hexane is analyzed after the preceding analysis and a carryover chlorpyrifos peak having 3 percent of the above-mentioned given area is observed.

COMPARATIVE EXAMPLE 4

The system of Example 3 is used except that the tubing from the check valve 50 to the tee 52 is blocked so that no gas can pass through it. The sample is hexane containing 50 parts per billion chlorpyrifos by weight. The sample is loaded into the valve 40, the Nelson system turns on the solenoid valve 46 and the sample within the channel 41a is injected into the at a pressure of about 10 psig. Two seconds later, the Nelson system turns off the solenoid valve 46 and the column head pressure remains at about 10 psig. The chlorpyrifos elutes from the column 54 and is detected by the detector 55 as a chromatographic peak of a given area. Another sample containing only hexane is analyzed after the preceding analysis and a carryover chlorpyrifos peak having 8 percent of the above-mentioned given area is observed.

What is claimed is:

1. A method for on-column valved injection gas chromatography with reduced analysis time, comprising the sequential steps of:
   (a) flowing a stream of gas through an injection valve, a capillary gas chromatography retention gap and a capillary gas chromatography column at a first flow rate;
   (b) injecting a predetermined volume of a liquid sample containing a solvent and a component of interest into the capillary gas chromatography retention gap using the injection valve, the predetermined volume being more than 5 microliters and less than 1 milliliter;
   (c) flowing a stream of gas through the capillary gas chromatography retention gap and the gas chromatography column at a second flow rate, the second flow rate being at least 50% higher than the first flow rate and the second flow rate being attained in less than about one second so that at least 50% of the solvent is moved through the capillary gas chromatography retention gap and the capillary gas chromatography column at at least a 50% increased rate;
   (d) flowing a stream of gas through the capillary gas chromatography retention gap and the capillary gas chromatography column at a third flow rate, the third flow rate being at least 50% lower than the second flow rate so that the component of interest can be chromatographed.

2. The method of claim 1, wherein in step (c) substantially all of the solvent is moved through the capillary gas chromatography retention gap and the capillary gas chromatography column.

3. The method of claim 2, wherein the predetermined volume of step (b) is determined by the dimensions of an injection loop of the injection valve.

4. The method of claim 3, wherein the first flow rate of step (a) is substantially equal to the third flow rate of step (d).

5. The method of claim 1, wherein in step (b) the liquid sample comprises an extractant exposed to one side of a two-sided membrane, the other side of the membrane exposed to a sample containing a component of interest, the component of interest permeating the membrane into the extractant.

6. The method of claim 5, wherein the two-sided membrane used is a tubular membrane.

7. The method of claim 6, wherein the tubular membrane used is a silicone rubber tubular membrane.

8. A method for on-column valved injection gas chromatography with reduced carryover, comprising the steps of:
  (a) flowing a stream of gas through an injection valve and a capillary gas chromatography column system at a first pressure;
  (b) injecting a predetermined volume of a liquid sample containing a solvent and a component of interest into the gas chromatography column system using the injection valve, the predetermined volume being less than 5 microliters;
  (c) simultaneously with step (b), flowing a stream of gas through the gas chromatography column system at a second pressure, the second pressure being at least 50% higher than the first pressure and the second pressure being attained in less than about one second so that the liquid sample is moved from the injection valve into the column system at an increased rate by the stream of gas;
  (d) flowing a stream of gas through the gas chromatography column system at a third pressure, the third pressure being at least 50% lower than the second pressure so that the component of interest can be chromatographed.

9. The method of claim 8, wherein the predetermined volume of step (b) is determined by the dimensions of a channel in a rotor of the injection valve.

10. The method of claim 8, wherein the first pressure of step (a) is substantially equal to the third pressure of step (d).

11. The method of claim 8, wherein the injection valve is gas operated by the same gas that is used in step (c).

* * * * *